(12) United States Patent
Peng et al.

(10) Patent No.: US 10,080,797 B2
(45) Date of Patent: Sep. 25, 2018

(54) ONCOLYTIC HETEROLOGOUS RECOMBINANT NEWCASTLE DISEASE VIRUS, PREPARATION METHOD AND APPLICATION THEREOF

(71) Applicant: Yongxiang Zhao, Changsha, Hunan (CN)

(72) Inventors: Xia Peng, Hunan (CN); Yi Peng, Guangxi (CN)

(73) Assignee: Yongxiang Zhao, Changsha (CN)

( * ) Notice: Subject to any disclaimer, the term of this patent is extended or adjusted under 35 U.S.C. 154(b) by 0 days.

(21) Appl. No.: 15/244,006

(22) Filed: Aug. 23, 2016

(65) Prior Publication Data

US 2017/0106079 A1 Apr. 20, 2017

Related U.S. Application Data

(63) Continuation of application No. PCT/CN2015/000024, filed on Jan. 13, 2015.

(30) Foreign Application Priority Data

Dec. 22, 2014 (CN) .......................... 2014 1 0803461

(51) Int. Cl.
| | |
|---|---|
| *A61K 31/702* | (2006.01) |
| *A61K 31/715* | (2006.01) |
| *A61K 35/18* | (2015.01) |
| *A61K 38/00* | (2006.01) |
| *A61K 38/14* | (2006.01) |
| *A61K 39/17* | (2006.01) |
| *C12N 7/00* | (2006.01) |
| *C12N 9/10* | (2006.01) |

(52) U.S. Cl.
CPC ................ *A61K 39/17* (2013.01); *C12N 7/00* (2013.01); *C12N 9/1051* (2013.01); *C12Y 204/01087* (2013.01); *C12N 2760/18121* (2013.01); *C12N 2760/18134* (2013.01)

(58) Field of Classification Search
CPC ........ C07K 14/005; C12N 2760/16122; C12N 2740/16122; C12N 7/00; A61K 2039/525
See application file for complete search history.

(56) References Cited

FOREIGN PATENT DOCUMENTS

| CN | 1704477 | * | 12/2005 |
|---|---|---|---|
| CN | 1704477 A | | 12/2005 |
| CN | 103352042 | * | 10/2013 |
| CN | 103352042 A | | 10/2013 |

OTHER PUBLICATIONS

McGregor et al., GenBank NP_998975.1, N-acetyllactosaminide alpha-1,3-galactosyltransferase, 2014:pdf pp. 1-3.*
International Search Report of PCT Patent Application No. PCT/CN2015/000024 dated Sep. 21, 2015.
McGregor, C.G. et al., NP_998975.1, N-acetyllactosaminide Alpha-1,3-galactosyltransferase [Sus scrota], GENBANK, Jan. 26, 2014.

* cited by examiner

*Primary Examiner* — Barry A Chestnut (57) ABSTRACT

Provided are an oncolytic heterologous recombinant Newcastle disease virus (NDV), preparation method and application thereof. The heterologous recombinant NDV can express alpha (1,3) galactosyltransferase (α1,3GT). The α1,3GT is the protein represented by the flowing B1) and B2): B1) the protein has an amino acid sequence of SEQ ID No.1; and B2) the protein is derived from B1) and has a function of α1,3GT obtained by substituting and/or deleting and/or adding one or more amino acid residue(s) in the amino acid sequence represented by SEQ ID No.1. The recombination NDV can be used for tumor treatment.

18 Claims, 3 Drawing Sheets

Specification includes a Sequence Listing.

Leader                                                                                       Trailer
3'—| NP |—| P |—| α-1,3GT |—| M |—| F |—| HN |—| L |—5'

ONCOLYTIC HETEROLOGOUS RECOMBINANT NEWCASTLE DISEASE VIRUS, PREPARATION METHOD AND APPLICATION THEREOF

CROSS REFERENCE TO RELATED APPLICATIONS

This application is a continuation application of PCT application No. PCT/CN2015/000024, which claims priority to Chinese Patent Application No. 201410803461.2 filed on Dec. 22, 2014, the entire contents of which are incorporated herein by reference.

REFERENCE TO SEQUENCE LISTING

The Sequence Listing is submitted concurrently with the specification as an ASCII formatted text file via EFS-Web, with a file name of "Substitute Sequence Listing v2.TXT", a creation date of Dec. 22, 2016, and a size of 24393 bytes. The Sequence Listing filed via EFS-Web is part of the specification and is incorporated in its entirety by reference herein.

TECHNICAL FIELD

This disclosure relates to oncolytic heterologous recombinant Newcastle disease virus and its preparation method and application in the biomedical field.

BACKGROUND

Newcastle disease virus (NDV) is capable of causing infection to a variety of poultries, while it has no pathogenicity to human. NDV, which belongs to the genus of Avulavirus in the Paramyxoviridae family, is a single-negative-stranded RNA virus, and it contains six independent transcription and coding units including nuclear protein (NP), phosphoprotein (P), matrix protein (M), fusion protein (F), hemagglutinin neuraminidase protein (HN) and large polymerase protein (L). A minimum infection unit of NDV is ribonucleoprotein composite, where genomic RNA, NP, P and L of NDV are assembled together into the infective ribonucleoprotein composite, thereby initiating preliminary transcription of the RNA as well as translation and synthesis of virus protein to generate infective progeny virus.

Reverse genetics is named with respect to classic genetics. Research strategy originating from genotype to phenotype of an organism, and various research techniques related thereto are generally named as reverse genetic techniques. The reverse genetic technique related to the RNA virus means that cloning for the infective molecule of the RNA virus were built in vitro, in which genomic RNA of the virus is reversedly transcribed into cDNA and various in vitro transformations, e.g., gene mutation, gene deletion, gene insertion, gene substitution, gene complementation and etc., are performed on the genome of the RNA virus at a DNA level, where such transformations are also called as "virus rescue".

Under the catalysis of α1,3galactosyltransferase (α1,3GT), glycosyl of uridine diphosphate galactose is transferred to N-acetyl glucosamine residue of chain of glycolipid and glycoprotein to form a α-galactosidase antigen (α-Gal antigen). α-Gal or Galα1-3Galβ1-4GlcNAc-R is a special carbohydrate structure, and α-galactosyl residue at its end is a natural specific recognition site for antigen since galactoses have to form α-connection at 1 and 3 sites therebetween.

SUMMARY OF THIS DISCLOSURE

The technical problem solved in this disclosure is how to achieve tumor treatment.

Recombinant Newcastle disease virus is first provided in this disclosure to solve such technical problem.

The recombinant Newcastle disease virus (recombinant NDV) provided in this disclosure can have an expression of α1,3galactosyltransferase (α1,3GT).

In such recombinant Newcastle disease virus, the expression of α1,3galactosyltransferase (α1,3GT) of the recombinant Newcastle disease virus means that, the recombinant Newcastle disease virus expresses the α1,3galactosyltransferase (α1,3GT) within cells, where the cells can be those capable of being infected by the Newcastle disease virus (NDV).

In such recombinant Newcastle disease virus, the α1,3galactosyltransferase (α1,3GT) is one of the following proteins B1) and B2):

B1) a protein with an amino acid sequence of SEQ ID No.1;

B2) a protein derived from B1) by replacing and/or deleting and/or adding one or more amino acid residue(s) in the amino acid sequence shown by the SEQ ID No.1, where the derived protein has the function of the α1,3galactosyltransferase (α1,3GT).

In such recombinant Newcastle disease virus, the recombinant Newcastle disease virus is a negative-stranded RNA virus, where an RNA complementary to the negative-stranded RNA (i.e., a positive-stranded RNA) is transcribed from the negative-stranded RNA of the recombinant Newcastle disease virus. The positive-stranded RNA contains RNAs that respectively code NP of the Newcastle disease virus, P of the Newcastle disease virus, M of the Newcastle disease virus, F of the Newcastle disease virus, HN of the Newcastle disease virus, L of the Newcastle disease virus and the α1,3galactosyltransferase.

In such recombinant Newcastle disease virus, the RNA that codes the α1,3galactosyltransferase is located between the RNAs that respectively code the P of the Newcastle disease virus and the M of the Newcastle disease virus.

In such recombinant Newcastle disease virus, a sequence of the positive-stranded RNA is obtained by replacing T with U and remaining other nucleotides unchanged in a sequence corresponding to SEQ ID No. 2 of a sequence table.

The SEQ ID No.2 is composed of 16332 nucleotides, where the $122^{nd}$-$1591^{st}$ nucleotides in the SEQ ID No.2 of the sequence table are a coding sequence of nuclear protein (NP) of the NDV; the $1893^{rd}$-$3080^{th}$ nucleotides in the SEQ ID No.2 are a coding sequence of phosphoprotein (P) of the NDV; the $4436^{th}$-$5530^{th}$ nucleotides in the SEQ ID No.2 are a coding sequence of matrix protein (M) of the NDV; the $5690^{th}$-$7351^{st}$ nucleotides in the SEQ ID No.2 are a coding sequence of fusion protein (F) of the NDV; the $7558^{th}$-$9273^{rd}$ nucleotides in the SEQ ID No.2 are a coding sequence of hemagglutinin neuraminidase protein (HN) of the NDV; the $9527^{th}$-$16141^{st}$ nucleotides in the SEQ ID No.2 are a coding sequence of large polymerase protein (L) of the NDV; the $3193^{rd}$-$4308^{th}$ nucleotides in the SEQ ID No.2 are a coding sequence of the α1,3galactosyltransferase (α1,3GT) that codes the protein shown by the SEQ ID No.1 of the sequence table.

In such recombinant Newcastle disease virus, genome of the recombinant Newcastle disease virus is a single-stranded ribonucleic acid which is obtained by replacing T with U and remaining other nucleotides unchanged in a reversed complementary strand with respect to the single strand shown by the SEQ ID No. 2.

Genome of the recombinant Newcastle disease virus is also provided in this disclosure to solve such technical problem.

The genome of the recombinant Newcastle disease virus is the genome of the above-described recombinant Newcastle disease virus.

Biological material related with the recombinant Newcastle disease virus is also provided in this disclosure to solve such technical problem.

The biological material related with the recombinant Newcastle disease virus in this disclosure refers to any one of the following materials E1)-E13).

E1) a recombinant vector containing DNA molecules for coding a positive-stranded RNA of the recombinant Newcastle disease virus;

E2) a recombinant microorganism containing DNA molecules for coding a positive-stranded RNA of the recombinant Newcastle disease virus;

E3) a recombinant microorganism containing the recombinant vector of E1);

E4) a transgenic animal cell line containing DNA molecules for coding a positive-stranded RNA of the recombinant Newcastle disease virus;

E5) a transgenic animal cell line containing the recombinant vector of E1);

E6) a transgenic animal tissue containing DNA molecules for coding a positive-stranded RNA of the recombinant Newcastle disease virus;

E7) a transgenic animal tissue containing the recombinant vector of E1);

E8) a transgenic animal organ containing DNA molecules for coding a positive-stranded RNA of the recombinant Newcastle disease virus;

E9) a transgenic animal organ containing the recombinant vector of E1);

E10) a microorganism containing the recombinant Newcastle disease virus;

E11) an animal cell line containing the recombinant Newcastle disease virus;

E12) an animal tissue containing the recombinant Newcastle disease virus;

E13) an animal organ containing the recombinant Newcastle disease virus.

In such biological material, the DNA molecules for coding the positive-stranded RNA of the recombinant Newcastle disease virus is those shown by the SEQ ID No. 2.

In such biological material, neither of the transgenic animal cell line, the transgenic animal tissue, the transgenic animal organ, the animal cell line, the animal tissue and the animal organ contains propagating material.

In such biological material, the recombinant microorganism of E2) can be the recombinant Newcastle disease virus.

In such biological material, the microorganism of E10), the animal cell line of E11), the animal tissue of E12) and the animal organ of E13) can all be a hose of the Newcastle disease virus.

A drug of any one of P1), P2) and P3 for treating and/or preventing tumor is also provided in this disclosure to solve such technical problem:

P1) a drug for treating and/or preventing tumor prepared using the recombinant Newcastle disease virus;

P2) a drug for treating and/or preventing tumor prepared using genome of the recombinant Newcastle disease virus;

P3) a drug for treating and/or preventing tumor prepared using biological material related with the recombinant Newcastle disease virus.

In such drug for treating and/or preventing tumor, an active ingredient in the drug of P1) can be the biological material related with the recombinant Newcastle disease virus.

An active ingredient in the drug of P2) can be the recombinant Newcastle disease virus.

Any of the following applications is provided in this disclosure to solve such technical problem:

I, the application of the recombinant Newcastle disease virus in preparing the drug for treating and/or preventing tumor;

II, the application of genome of the recombinant Newcastle disease virus in preparing the drug for treating and/or preventing tumor;

III, the application of the biological material related with the recombinant Newcastle disease virus in preparing the drug for treating and/or preventing tumor.

The following method for treating and/or preventing mammal tumor is also included in the protection scope of this disclosure.

The method for treating and/or preventing mammal tumor of this disclosure includes applying the drug for treating and/or preventing tumor onto an animal as a receptor.

The following method for treating and/or preventing mammal tumor is also included in the protection scope of this disclosure.

The method for treating and/or preventing mammal tumor of this disclosure includes applying any one of the following M1)-M3) onto an animal as a receptor:

M1) the recombinant Newcastle disease virus;

M2) the genome of the recombinant Newcastle disease virus;

M3) the biological material related with the recombinant Newcastle disease virus.

Any of the following applications is within the protection scope of this disclosure:

N1) the application of the recombinant Newcastle disease virus in treating and/or preventing mammal tumor;

N2) the application of the genome of the recombinant Newcastle disease virus in treating and/or preventing mammal tumor;

N3) the application of the biological material related with the recombinant Newcastle disease virus in treating and/or preventing mammal tumor.

The tumor in this disclosure can be malignant tumor, such as lung cancer and/or breast cancer and/or liver cancer and/or intestinal cancer and/or prostate cancer and/or pancreatic cancer and/or leukemia.

The mammal of this disclosure can be human (*Homo sapiens*).

The vector for the gene of the recombinant α1,3galactosyltransferase (α1,3GT) in this disclosure can be any pathogenic microorganism including the NDV.

BRIEF DESCRIPTION OF THE DRAWINGS

FIGS. 3A and 3B illustrate an expression result for α1,3GT of an NDV/α1,3GT, where FIG. 3A shows an immunofluoresence test result for A549 infected by the NDV/α1,3GT.

DETAILED DESCRIPTION

Below this disclosure is further described in detail with reference to specific implementations. Those embodiments herein are merely for explaining this disclosure rather than limiting the scope of this disclosure.

Those experimental methods in the following embodiments can be corresponding conventional methods without special definition.

Those materials and reagents used in the following embodiments can be commercially purchased without special definition.

Those SCID mice in the following embodiments are obtained from Beijing Weitonglihua Experimental Animal Technology Co., Ltd.

Those hepatoma carcinoma cells HepG2 in the following embodiments are purchased from ATCC cell bank with an article number of HB-8065™.

Those human lung adenocarcinoma cells A549 in the following embodiments are purchased from ATCC cell bank with an article number of CCL-185™.

Those transcription vectors TVT/071204, pCI-NP, pCI-P, pCI-L, BSR-T7/5 and a strain of Newcastle disease virus (NDV) JS/07/04/Pi in the following embodiments (Construction and Rescue of infectious cDNA Clone of Pigeon-Origin Newcastle Disease Virus Strain JS/07/04/Pi, Chinese Journal of Virolory, 2012, 28(1):67-72.) are gifted from a key open laboratory of livestock and poultry epidemiology of Ministry of Agriculture. These biological materials are only used for relevant experiments in this disclosure, while they can not be used for any other purposes. The transcription vector TVT/071204 contains full-length cDNA of genome of the strain of Newcastle disease virus (NDV) JS/07/04/Pi.

PBS in the following embodiments is 0.01M PBS (Ph 7.2), and its preparation method is as follows: dissolving 8.00 g sodium chloride (NaCl), 0.20 g potassium chloride (KCl), 1.44 g disodium hydrogen phosphate ($Na_2HPO_4$) and 0.24 g potassium phosphate monobasic $KH_2PO_4$ in 800 mL deionized water, regulating by concentrated hydrochloric acid pH value of the solution to pH 7.2, adding deionized water to 1 L and performing autoclaved sterilization on the solution (121° C., 15-20 min).

ISOLECTIN GS-IB4 in the following embodiments is a product with an article number of I32450 from Invitrogen Company. The ISOLECTIN GS-IB4 here is bonded with Alexa Fluor® 647.

First Embodiment: Recombinant Newcastle Disease Virus (Recombinant NDV) and its Function 1. Preparation of Recombinant Newcastle Disease Virus.

The recombinant NDV carrying α1,3GT gene is constructed by reference to methods in the following literatures including Rescue and Preliminary Application of a Recombinant Newcastle Disease Virus Expressing Green Fluorescent Protein Gene, Virologica Sinica, 2007, 22 (1):34-40 and Construction and Rescue of infectious cDNA Clone of Pigeon-Origin Newcastle Disease Virus Strain JS/07/04/Pi, Chinese Journal of Virolory, 2012, 28(1):67-72. Specifically, α1,3GT gene of a pig is cloned to genome of TVT/071204 to obtain recombinant vector TVT07+α. Co-transfection through three helper plasmids pCI-NP, pCI-P and pCI-L and the recombinant vector TVT07+α is carried out for BSR-T7/5 cells, which are then transferred after the 60 h co-transfection to repeated freeze thawing for three times at −70° C. After that, the frozen and thawed cells and their supernatants are used to inoculate SPF chick embryo of 9-11 days-age according to 0.2 ml/embryo, and the chick embryo becoming dead within 24 hours is discarded. Allantoic fluid of the chick embryo that dies after 24 hours is collected, and both hemagglutination (HA) test and hemagglutination inhibition (HI) test are performed according to OIE standards on the collected allantoic fluid. The samples having positive HA test result and HI test result contain the recombinant Newcastle disease virus (recombinant NDV) that are saved successively.

The allantoic fluid having positive HA test result and HI test result is propagated on the SPF chick embryo for three generations. The allantoic fluid is then collected to obtain the recombinant Newcastle disease virus (recombinant NDV) expressing α1,3GT gene, which is called as NDV/α1,3GT.

2. RT-PCR of NDV/α1,3GT.

Figure 1:
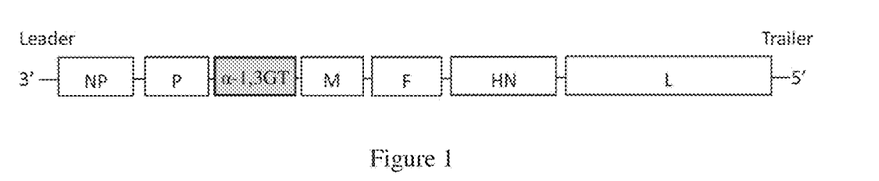
FIG. 1 schematically illustrates an NDV/α1,3GT having an inserted α1,3GT gene.
Figure 2:
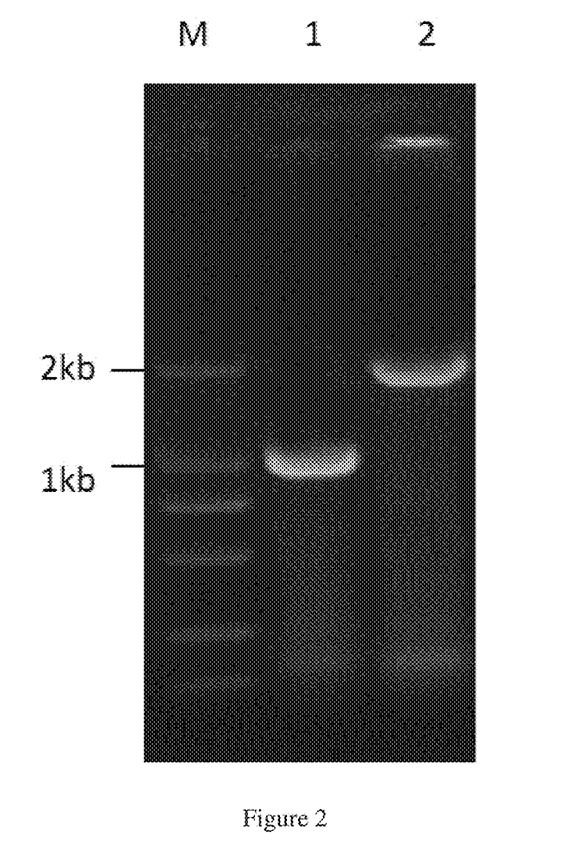
FIG. 2 illustrates an RT-PCR result for an NDV/α1,3GT, where an electrophoresis lane M represents a DNA marker DL2000, an electrophoresis lane 1 represents a strain of Newcastle disease virus (NDV) JS/07/04/Pi, and an electrophoresis lane 2 represents the NDV/α1,3GT.

RNA of the NDV/α1,3GT is extracted according to an instruction of Trizol reagent to obtain total RNA of the NDV/α1,3GT. Reverse transcription is carried out taking the total RNA of the NDV/α1,3GT as a template to obtain NDV/α1,3GT cDNA. Total RNA of the strain of Newcastle disease virus (NDV) JS/07/04/Pi is extracted to obtain the total RNA of the NDV. Another reverse transcription is carried out taking the total RNA of the NDV as a template to obtain NDV cDNA. PCR is performed using the NDV/α1,3GT cDNA and NDV cDNA as the template and using P1-1: 5'-GACACAGAGGGGTGAAATGACACTC-3' and P3-2: 5'-TAGACATCCTTCCTCGGCACTACAGT-3' as a primer pair, where an amplification product is analyzed using 1% agarose gel electrophoresis. The analysis result is shown in FIG. 2, where an electrophoresis lane M represents a DNA marker DL2000, an electrophoresis lane 1 represents a PCR product of cDNA of the strain of Newcastle disease virus (NDV) JS/07/04/Pi of which a target fragment size is about 1 kb, and an electrophoresis lane 2 represents a PCR product of cDNA of the NDV/α1,3GT of which a target fragment size is about 2 kb. The amplification products are collected for sequencing, where the sequencing result shows that the genome of NDV/α1,3GT is a single-stranded ribonucleic acid which is obtained by replacing T with U and remaining other nucleotides unchanged in a reversed complementary strand with respect to the single-stranded ribonucleic acid shown by SEQ ID No. 2, where the α1,3GT gene is successively inserted between P and M of the NDV, and its insert location is shown in FIG. 1. Here, SEQ ID No.2 is composed of 16332 nucleotides, where the $122^{nd}$-$1591^{st}$ nucleotides in the SEQ ID No.2 of the sequence table are a coding sequence of nuclear protein (NP) of the NDV; the $1893^{rd}$-$3080^{th}$ nucleotides in the SEQ ID No.2 are a coding sequence of phosphoprotein (P) of the NDV; the $4436^{th}$-$5530^{th}$ nucleotides in the SEQ ID No.2 are a coding sequence of matrix protein (M) of the NDV; the $5690^{th}$-$7351^{st}$ nucleotides in the SEQ ID No.2 are a coding sequence of fusion protein (F) of the NDV; the $7558^{th}$-$9273^{rd}$ nucleotides in the SEQ ID No.2 are a coding sequence of hemagglutinin neuraminidase protein (HN) of the NDV; the $9527^{th}$-$16141^{st}$ nucleotides in the SEQ ID No.2 are a coding sequence of large polymerase protein (L) of NDV; the $3193^{rd}$-$4308^{th}$ nucleotides in the SEQ ID No.2 are a coding sequence of α1,3galactosyltransferase (α1,3GT) that codes the protein shown by SEQ ID No.1 of the sequence table.

The NDV/α1,3GT is a negative-stranded RNA virus, where an RNA complementary to the negative-stranded RNA (i.e., a positive-stranded RNA) is transcribed based on the negative-stranded RNA of the NDV/α1,3GT. The positive-stranded RNA contains RNA molecules that respectively code NP of the Newcastle disease virus, P of the Newcastle disease virus, M of the strain of Newcastle disease virus, F of the strain of Newcastle disease virus, HN of the strain of Newcastle disease virus, L of the strain of Newcastle disease virus and the α1,3galactosyltransferase, where the α1,3galactosyltransferase is the protein having the amino acid sequence of the SEQ ID No.1.

3. Expression of α1,3GT of the NDV/α1,3GT.

The NDV/α1,3GT of the step 1 is inoculated into human lung adenocarcinoma cells A549 to obtain the A549 cells infected by the NDV/α1,3GT. The strain of Newcastle disease virus (NDV) JS/07/04/Pi is also inoculated into the human lung adenocarcinoma cells A549 to obtain the A549 cells infected by the NDV. The expression of the α1,3GT within the A549 cells infected by the recombinant Newcastle disease virus is detected using an immumofluorescence method, and includes the following steps:

1) 1 mg/mL ISOLECTIN GS-IBS is prepared by dissolving 500 μg ISOLECTIN GS-IB4 using 500 μL diluents, where the diluents (pH 7.2) are 0.01 M PBS containing 1.0 mM $CaCl_2$ and 2 mM sodium azide. The 1 mg/mL ISOLECTIN GS-IBS is subpackaged per 5 μL or 10 μL, and it is kept in dark place at −20° C. to avoid repeated freeze thawing. The ISOLECTIN GS-IBS is dissolved and centrifuged immediately before its usage, and the supernatant is diluted by 100 times using the 0.01M PBS to obtain the diluted GS-IB4. It is noted that those operations are performed in a dark condition.

2) $1\times10^5$ A549 cells are tiled within a confocal dedicated vessel (which is a culture dish with a glass bottom of 35 mm, an aperture of 10 mm and a glass thickness of 0.085-0.13 mm). When the cell density becomes 60%-70% of the vessel bottom, the NDV/α1,3GT of the step 1 is inoculated. After the cells are infected by the virus for 60 h, the A549 cells infected by the NDV/α1,3GT are obtained. The A549 cells infected by the NDV/α1,3GT are taken out of an incubator, the culture medium is discarded, the cells are washed for two times using PBS (while being cautious of cell dropping) and then fixed by 4% paraformaldehyde (which covers the whole bottom of the confocal vessel) for 20 min under the room temperature, where the fixed cells are washed by the PBS for three times (3 min/time).

3) 0.2% Triton X-100 is added till covering the whole bottom of the confocal vessel, and permeabilization lasts for 10 min. After that, the vessel is washed using the 1×PBS for three times (3 min/time).

4) 2% calf serum is added (which covers the whole bottom of the confocal vessel) for blocking the cells for 30 min under the room temperature.

5) The blocking liquid is discarded and the cells are washed using the PBS for three times (3 min/time). The diluted GS-IB4 is added till covering the whole bottom of the confocal vessel, and the cells are incubated within a humid box for 3 h at 4° C. A blank control group is added with PBS to replace the dilute GS-IB4. The addition of the diluted GS-IB4 and the PBS should be performed in a dark environment. The cells are then washed using PBS for three times (5 min/time) in a dark environment.

6) Those cells are observed and photographed under a confocal fluorescence microscope.

According to such immumofluorescence method contains step 1)-6), the NDV/α1,3GT is replaced by the strain of Newcastle disease virus (NDV) JS/07/04/Pi to act as the negative control group.

Figure 3A:
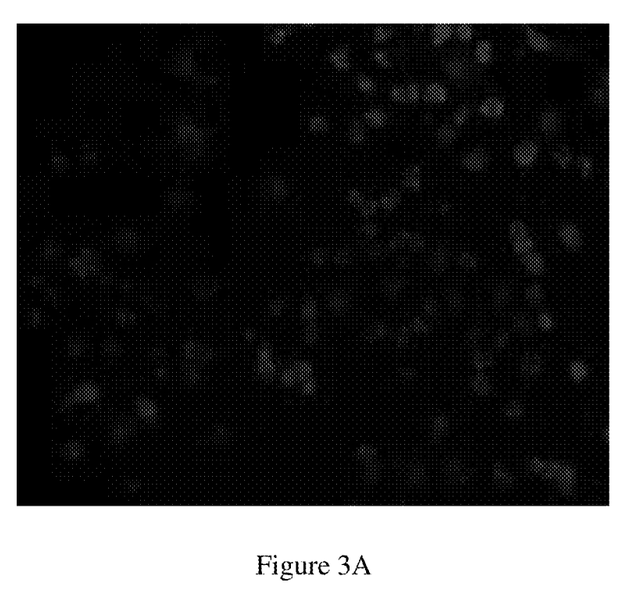
Figure 3B:
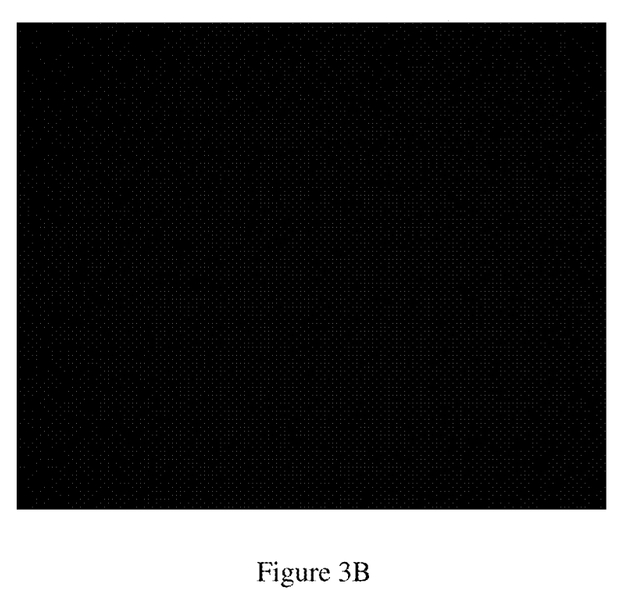
FIG. 3B shows an immunofluoresence test result for A549 infected by the strain of Newcastle disease virus (NDV) JS/07/04/Pi.

The α1,3GT expressed in the A549 cells infected by the NDV/α1,3GT may be catalyzed to generate α-Gal, where α-Gal can be bonded with the lectin ISOLECTIN GS-IB4 marked by Alexa Fluor® 647 to emit red fluorescence (A in FIGS. 3A and 3B). There is no fluorescence in the negative control group (B in FIGS. 3A and 3B). Those results indicate that the A549 cells infected by the NDV/α1,3GT express the α1,3GT protein.

Second Embodiment: Lethal Effect of NDV/α1,3GT on Tumor Cells

The tests are repeated for three times. Specific steps for each test are described below.

Figure 4:
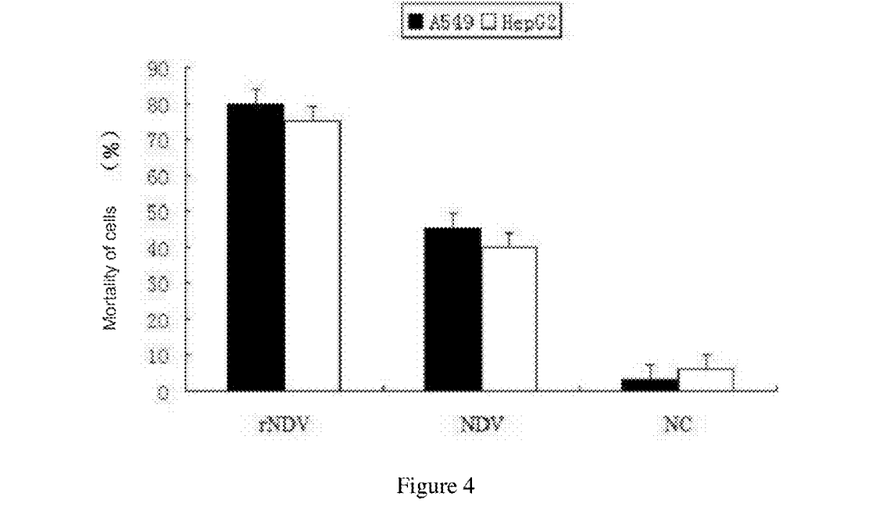
FIG. 4 illustrates respective lethal ratios of an NDV/α1, 3GT for killing human lung adenocarcinoma cells A549 and hepatoma carcinoma cells HepG2, where rNDV represents the NDV/α-1,3GT, NC represents a negative control, and NDV represents a strain of Newcastle disease virus (NDV) JS/07/04/Pi.

Trypsinization is carried out on the human lung adenocarcinoma cells A549 to obtain dissociated A549. The cell density is adjusted using cell counting. The dissociated A549 cells are inoculated to a 48-well plate with DMEM culture medium containing 10% fetal calf serum according to a standard of $5\times10^4$ cells in each well, and are cultured within an incubator at 37° C. for 24 h. The A549 cells are respectively inoculated according to 0.25 MOI with the NDV/α1,3GT and the strain of Newcastle disease virus (NDV) JS/07/04/Pi in the first embodiment, while the cells without virus inoculation are used as the negative control group. After the virus inoculation for 5 h, 200 μl human serum is added into each well; the cells are cultured at 37° C. for 48 h within the incubator, and trypan blue staining is performed for the cells for cell counting, so as to calculate the lethal ratio of the NDV/α1,3GT on the A549 cells (i.e., cell death rate) (FIG. 4).

The human lung adenocarcinoma cells A549 are replaced by hepatoma carcinoma cells HepG2, while other operations remain unchanged as the second embodiment. The lethal ratio of the NDV/α1,3GT on the hepatoma carcinoma cells HepG2 is calculated (FIG. 4).

The test results show, the lethal ratios of the NDV/α1,3GT on the A549 cells and the HepG2 cells are respectively 79.8% and 75%; the lethal ratios of the strain of Newcastle disease virus (NDV) JS/07/04/Pi on the A549 cells and the HepG2 cells are respectively 45.2% and 40%. The death rates of the A549 cells and the HepG2 cells in the negative control group are respectively 3.2% and 6%. The lethal ratio of the NDV/α1,3GT on the A549 cells is 1.76 times higher than that of the strain of Newcastle disease virus (NDV)

JS/07/04/Pi, and the lethal ratio of the NDV/α1,3GT on the HepG2 cells is 1.88 times higher than that of the strain of Newcastle disease virus (NDV) JS/07/04/Pi. Those test results show that the NDV/α1,3GT has better lethal effect on the tumor cells.

Third Embodiment, Treatment Effect of Recombinant NDV on Tumor

Human immune system is reconstructed for SCID mice that are then inoculated with the human lung adenocarcinoma cells A549. The SCID mice with reconstructed human immune system and inoculated human lung cancer are treated by the NDV/α1,3GT. This experiment is repeated for three times, while specific steps for the experiment are described below.

The NDV/α1,3GT of the first embodiment is re-suspended using the PBS to obtain an NDV/α1,3GT suspension liquid with a titer of $2.5 \times 10^5$ pfu/100 μl. The strain of Newcastle disease virus (NDV) JS/07/04/Pi is re-suspended using the PBS to obtain a JS/07/04/Pi suspension liquid with a titer of $2.5 \times 10^5$ pfu/100 μl.

Figure 5:
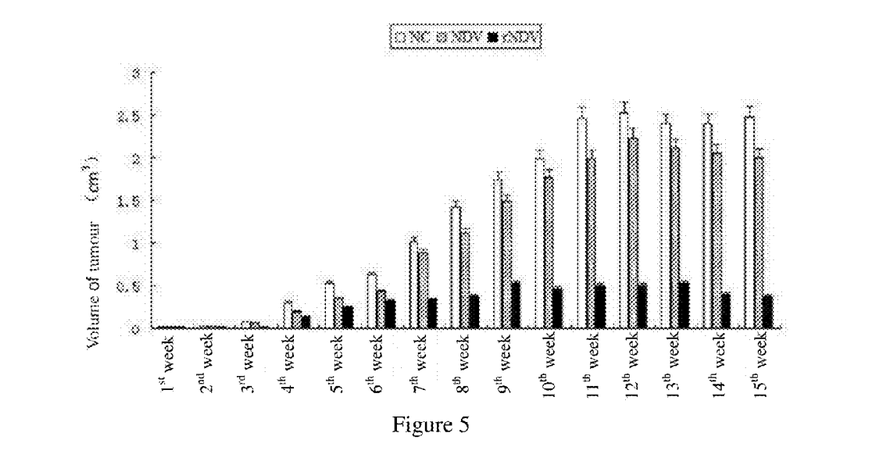
FIG. 5 illustrates tumor treatment effect of an NDV/α1, 3GT on SCID mice having reconstructed human immune system and human lung adenocarcinoma, where rNDV represents the NDV/α1,3GT, NC represents a PBS control, and NDV represents a strain of Newcastle disease virus (NDV) JS/07/04/Pi.

Hypodermic inoculation is performed at a right underarm for each of twenty 6-week-aged SCID mice, where $1 \times 10^7$ human lung adenocarcinoma cells A549 are inoculated into each SCID mouse. A major axis and a minor axis of the tumor are measured twice every week, and a volume of the tumor is calculated following a formula $TV = 1/2 \times a \times b^2$. After the human lung adenocarcinoma cells A549 have been inoculated for 15 days, 100 μl NDV/α1,3GT suspension liquid (which has a titer of $2.5 \times 10^5$ pfu/100 μl for the NDV/α1,3GT therein) is injected into each mouse through its caudal vein. The day on which the NDV/α1,3GT is injected for the first time is recorded as $0^{th}$ treatment day. On a $3^{rd}$ treatment day, $1 \times 10^7$ human peripheral blood lymphocytes (PBMC) are injected into each mouse through intraperitoneal injection, and 200 μl human serum is injected into each mouse through its caudal vein. 100 μl NDV/α1,3GT suspension liquid (which has a titer of $2.5 \times 10^5$ pfu/100 μl for the NDV/α1,3GT) is respectively injected into each mouse through its caudal vein on a $10^{th}$ treatment day, a $14^{th}$ treatment day and a $21^{st}$ treatment day. $1 \times 10^7$ human peripheral blood lymphocytes (PBMC) are respectively injected into each mouse through intraperitoneal injection and 200 μl human serum is injected into each mouse through its caudal vein on a $10^{th}$ treatment day, a $17^{th}$ treatment day and a $24^{th}$ treatment day. The tumor volume (cm³) is recorded for each mouse from the $0^{th}$ treatment day (i.e., the $1^{st}$ week), and the tumor volume (cm³) is measured for each mouse on a $7^{th}$ treatment day (i.e., the $2^{nd}$ week), a $14^{th}$ treatment day (i.e., the $3^{rd}$ week), a $24^{th}$ treatment day (i.e., the $4^{th}$ week), a $28^{th}$ treatment day (i.e., the $5^{th}$ week), a $35^{th}$ treatment day (i.e., the $6^{th}$ week), a $42^{nd}$ treatment day (i.e., the $7^{th}$ week), a $49^{th}$ treatment day (i.e., the $8^{th}$ week), a $56^{th}$ treatment day (i.e., the $9^{th}$ week), a $63^{rd}$ treatment day (i.e., the $10^{th}$ week), a $70^{th}$ treatment day (i.e., the $11^{th}$ week), a $77^{th}$ treatment day (i.e., the $12^{th}$ week), a $84^{th}$ treatment day (i.e., the $13^{th}$ week), a $91^{st}$ treatment day (i.e., the $14^{th}$ week) and a $98^{th}$ treatment day (i.e., the $15^{th}$ week). Average tumor volumes when the NDV/α1,3GT is used to treat the tumor are shown in FIG. 5 and table 1.

The NDV/α1,3GT suspension liquid is replaced by the JS/07/04/Pi suspension liquid, while other operations remain unchanged as the third embodiment. Average tumor volumes when treating the tumor with the JS/07/04/Pi suspension liquid are recorded (FIG. 5 and table 1).

The NDV/α1,3GT suspension liquid is replaced by the PBS, while other operations remain unchanged as the third embodiment. Average tumor volumes when treating the tumor with the PBS are recorded (FIG. 5 and table 1).

Table 1, treatment effect of NDV/α1,3GT on SCID mice with reconstructed human immune system and inoculated human lung cancer (cm³)

| Treatment Time | PBS | Strain of Newcastle disease virus (NDV) JS/07/04/Pi | NDV/α1,3GT |
| --- | --- | --- | --- |
| $1^{st}$ week | 0.009755 | 0.008795 | 0.008125 |
| $2^{nd}$ week | 0.02872 | 0.01972 | 0.01404 |
| $3^{rd}$ week | 0.078 | 0.058 | 0.01404 |
| $4^{th}$ week | 0.29952 | 0.196 | 0.13104 |
| $5^{th}$ week | 0.52 | 0.345 | 0.24206 |
| $6^{th}$ week | 0.624 | 0.43 | 0.31616 |
| $7^{th}$ week | 1.01088 | 0.879 | 0.3328 |
| $8^{th}$ week | 1.42155 | 1.11 | 0.36608 |
| $9^{th}$ week | 1.74928 | 1.489 | 0.5265 |
| $10^{th}$ week | 1.989 | 1.769 | 0.46332 |
| $11^{th}$ week | 2.46272 | 1.99 | 0.50544 |
| $12^{th}$ week | 2.52928 | 2.234 | 0.50544 |
| $13^{th}$ week | 2.39616 | 2.11 | 0.5265 |
| $14^{th}$ week | 2.39616 | 2.05 | 0.39936 |
| $15^{th}$ week | 2.477475 | 2 | 0.36608 |

The calculation results show that, the volume of the tumor that is treated by the strain of Newcastle disease virus (NDV) JS/07/04/Pi for 15 weeks is 5.46 times larger than that of the tumor treated by the NDV/α1,3GT, and the volume of the tumor that is treated by the PBS for 15 weeks is 6.77 times larger than that of the tumor treated by the NDV/α1,3GT. Therefore, the NDV/α1,3GT can treat the tumor.

INDUSTRIAL APPLICATION

The recombinant NDV in this disclosure has stronger lethal effect on tumor cells: the lethal effects on A549 cells and the HepG2 cells of the recombinant NDV are 1.76 times and 1.88 times higher than those of NDV. The recombinant NDV in this disclosure can treat the tumor: the volume of the tumor that is treated by NDV is 5.46 times larger than that of the tumor treated by the recombinant NDV, and the volume of the tumor that is treated by the PBS is 6.77 times larger than that of the tumor treated by the recombinant NDV. Those experiments prove that the recombinant NDV of this disclosure can be used for tumor treatment.

The invention claimed is:

1. A recombinant Newcastle disease virus that has an expression of α1,3galactosyltransferase (α1,3 GT);

the recombinant Newcastle disease virus is a negative-stranded RNA virus; an RNA complementary to the negative-stranded RNA is transcribed from the negative-stranded RNA of the recombinant Newcastle disease virus, wherein the complementary RNA is a positive-stranded RNA that contains RNA for coding NP of the Newcastle disease virus, RNA for coding P of the Newcastle disease virus, RNA for coding M of the Newcastle disease virus, RNA for coding F of the Newcastle disease virus, RNA for coding HN of the Newcastle disease virus, RNA for coding L of the Newcastle disease virus and RNA for coding the α1,3galactosyltransferase.

2. The recombinant Newcastle disease virus of claim 1, wherein the α1,3galactosyltransferase (α1,3GT) is one of following proteins B1) and B2):

B1) a protein with an amino acid sequence of SEQ ID No.1;

B2) a protein derived from B1) by replacing and/or deleting and/or adding one amino acid residue in the amino acid sequence shown by the SEQ ID No.1, wherein the derived protein has the function of the α1,3galactosyltransferase (α1,3GT).

3. The recombinant Newcastle disease virus of claim 1, wherein the RNA that codes the α1,3galactosyltransferase is located between the RNAs that respectively code the P of the Newcastle disease virus and the M of the Newcastle disease virus.

4. The recombinant Newcastle disease virus of claim 1, wherein a sequence of the positive-stranded RNA is obtained by replacing T with U and remaining other nucleotides unchanged in a sequence corresponding to SEQ ID No. 2 of a sequence table.

5. The recombinant Newcastle disease virus of claim 1, wherein a genome of the recombinant Newcastle disease virus is a single-stranded ribonucleic acid which is obtained by replacing T with U and remaining other nucleotides unchanged in a reversed complementary strand with respect to a single strand shown by SEQ ID No. 2.

6. A genome of a recombinant Newcastle disease virus of claim 1; wherein the recombinant Newcastle disease virus is a negative-stranded RNA virus; an RNA complementary to the negative-stranded RNA is transcribed from the negative-stranded RNA of the recombinant Newcastle disease virus, wherein the complementary RNA is a positive-stranded RNA that contains RNA for coding NP of the Newcastle disease virus, RNA for coding P of the Newcastle disease virus, RNA for coding M of the Newcastle disease virus, RNA for coding F of the Newcastle disease virus, RNA for coding HN of the Newcastle disease virus, RNA for coding L of the Newcastle disease virus and RNA for coding the α1,3galactosyltransferase.

7. The genome of claim 6, wherein the α1,3galactosyltransferase (α1,3GT) is one of following proteins B1) and B2):

B1) a protein with an amino acid sequence of SEQ ID No.1;

B2) a protein derived from B1) by replacing and/or deleting and/or adding one amino acid residue in the amino acid sequence shown by the SEQ ID No.1, wherein the derived protein has the function of the α1,3galactosyltransferase (α1,3GT).

8. The genome of claim 1, wherein the RNA that codes the α1,3galactosyltransferase is located between the RNAs that respectively code the P of the Newcastle disease virus and the M of the Newcastle disease virus.

9. The genome of claim 1, wherein a sequence of the positive-stranded RNA is obtained by replacing T with U and remaining other nucleotides unchanged in a sequence corresponding to SEQ ID No. 2 of a sequence table.

10. The genome of claim 6, wherein a sequence of the genome of the recombinant Newcastle disease virus is a single-stranded ribonucleic acid which is obtained by replacing T with U and remaining other nucleotides unchanged in a reversed complementary strand with respect to a single strand shown by SEQ ID No. 2.

11. A vaccine for treating and/or preventing tumor of any of P1)-P4):

P1) a vaccine for treating and/or preventing tumor prepared using the recombinant Newcastle disease virus of claim 1;

P2) a vaccine for treating and/or preventing tumor prepared using the genome of the recombinant Newcastle disease virus of claim 1;

P3) a vaccine for treating and/or preventing tumor prepared using a recombinant vector containing DNA molecules for coding a positive-stranded RNA of the recombinant Newcastle disease virus of claim 1, a recombinant microorganism containing the recombinant vector having DNA molecules for coding a positive-stranded RNA, a recombinant microorganism containing DNA molecules for coding a positive-stranded RNA, a transgenic animal cell line containing DNA molecules for coding a positive-stranded RNA, a transgenic animal cell line containing the recombinant vector having DNA molecules for coding a positive-stranded RNA, a transgenic animal tissue containing DNA molecules for coding a positive-stranded RNA, a transgenic animal tissue containing the recombinant vector having DNA molecules for coding a positive-stranded RNA, a transgenic animal organ containing DNA molecules for coding a positive-stranded RNA, and/or a transgenic animal organ containing the recombinant vector having DNA molecules for coding a positive-stranded RNA;

P4) a vaccine for treating and/or preventing tumor prepared by microorganism, animal cell line, animal tissue and/or tissue organ containing the recombinant Newcastle disease virus of claim 1.

12. A drug for treating and/or preventing tumor of any of P1)-P4):

P1) a drug for treating and/or preventing tumor prepared using the recombinant Newcastle disease virus of claim 1;

P2) a drug for treating and/or preventing tumor prepared using the genome of the recombinant Newcastle disease virus of claim 1;

P3) a drug for treating and/or preventing tumor prepared using a recombinant vector containing DNA molecules for coding a positive-stranded RNA of the recombinant Newcastle disease virus of claim 1, a recombinant microorganism containing the recombinant vector having DNA molecules for coding a positive-stranded RNA, a recombinant microorganism containing DNA molecules for coding a positive-stranded RNA, a transgenic animal cell line containing DNA molecules for coding a positive-stranded RNA, a transgenic animal cell line containing the recombinant vector having DNA molecules for coding a positive-stranded RNA, a transgenic animal tissue containing DNA molecules for coding a positive-stranded RNA, a transgenic animal tissue containing the recombinant vector having DNA molecules for coding a positive-stranded RNA, a transgenic animal organ containing DNA molecules for coding a positive-stranded RNA, and/or a transgenic animal organ containing the recombinant vector having DNA molecules for coding a positive-stranded RNA;

P4) a drug for treating and/or preventing tumor prepared by microorganism, animal cell line, animal tissue and/or tissue organ containing the recombinant Newcastle disease virus of claim 1.

13. The drug for treating and/or preventing tumor of claim 12, wherein the tumor comprises malignant solid tumor including lung cancer and/or liver cancer and/or prostate cancer and/or pancreatic cancer, and comprises blood cancer including leukemia.

14. The drug for treating and/or preventing tumor of claim 12, wherein the α1,3galactosyltransferase (α1,3GT) is one of following proteins B1) and B2):

B1) a protein with an amino acid sequence of SEQ ID No.1;

B2) a protein derived from B1) by replacing and/or deleting and/or adding one or more amino acid residue in the amino acid sequence shown by the SEQ ID No.1, wherein the derived protein has the function of the α1,3galactosyltransferase (α1,3GT).

15. The drug for treating and/or preventing tumor of claim 12, wherein the RNA that codes the α1,3galactosyltransferase is located between the RNAs that respectively code the P of the Newcastle disease virus and the M of the Newcastle disease virus.

16. The drug for treating and/or preventing tumor of claim 12, wherein a sequence of the positive-stranded RNA is obtained by replacing T with U and remaining other nucleotides unchanged in a sequence corresponding to SEQ ID No. 2 of a sequence table.

17. The drug for treating and/or preventing tumor of claim 12, wherein a sequence of the genome of the recombinant Newcastle disease virus is a single-stranded ribonucleic acid which is obtained by replacing T with U and remaining other nucleotides unchanged in a reversed complementary strand with respect to a single strand shown by SEQ ID No. 2.

18. The drug for treating and/or preventing tumor of claim 12, wherein the recombinant vector is pathogenic microorganism for recombining α1,3galactosyltransferase gene; the tumor comprises malignant tumor including lung cancer and/or breast cancer and/or liver cancer and/or intestinal cancer and/or prostate cancer and/or pancreatic cancer and/or leukemia.

* * * * *

SEQUENCE LISTING

<160> NUMBER OF SEQ ID NOS: 2

<210> SEQ ID NO 1
<211> LENGTH: 371
<212> TYPE: PRT
<213> ORGANISM: Artificial Sequence
<220> FEATURE:
<223> OTHER INFORMATION: Synthetic

<400> SEQUENCE: 1

Met Asn Val Lys Gly Arg Val Val Leu Ser Met Leu Leu Val Ser Thr
1               5                   10                  15

Val Met Val Val Phe Trp Glu Tyr Ile Asn Ser Pro Glu Gly Ser Leu
            20                  25                  30

Phe Trp Ile Tyr Gln Ser Lys Asn Pro Glu Val Gly Ser Ser Ala Gln
        35                  40                  45

Arg Gly Trp Trp Phe Pro Ser Trp Phe Asn Asn Gly Thr His Ser Tyr
    50                  55                  60

His Glu Glu Glu Asp Ala Ile Gly Asn Glu Lys Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
            100                 105                 110

Glu Gly Thr Tyr Asn Arg Ala Val Leu Asp Asn Tyr Tyr Ala Lys Gln
        115                 120                 125

Lys Ile Thr Val Gly Leu Thr Val Phe Ala Val Gly Arg Tyr Ile Glu
    130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                165                 170                 175

Pro Leu Ile Glu Leu Gly Pro Leu Arg Ser Phe Lys Val Phe Glu Ile
            180                 185                 190

Lys Ser Glu Lys Arg Trp Gln Asp Ile Ser Met Met Arg Met Lys Thr
        195                 200                 205

Ile Gly Glu His Ile Leu Ala His Ile Gln His Glu Val Asp Phe Leu
    210                 215                 220

Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
                245                 250                 255

His Pro Asp Glu Phe Thr Tyr Glu Arg Arg Lys Glu Ser Ala Ala Tyr
            260                 265                 270

Ile Pro Phe Gly Gln Gly Asp Phe Tyr Tyr His Ala Ala Ile Phe Gly
        275                 280                 285

Gly Thr Pro Thr Gln Val Leu Asn Ile Thr Gln Glu Cys Phe Lys Gly
    290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
                325                 330                 335

Ser Pro Glu Tyr Cys Trp Asp Tyr His Ile Gly Met Ser Val Asp Ile
            340                 345                 350

Arg Ile Val Lys Ile Ala Trp Gln Lys Lys Glu Tyr Asn Leu Val Arg
        355                 360                 365

Asn Asn Ile
    370

<210> SEQ ID NO 2

<211> LENGTH: 16332
<212> TYPE: DNA
<213> ORGANISM: Artificial Sequence
<220> FEATURE:
<223> OTHER INFORMATION: Synthetic

<400> SEQUENCE: 2

```
accaaacaga gaatccgtga gttacggtaa agggcgaata agcaatcgaa atcgcacggg      60
tagaaggtgt gaacctcgag tgcgaggccg agactcaaac ctgagggaac cttctgccgg     120
catgtcatcc gtctttgacg aatacgagca gctgcttgct gctcagactc gccctaatgg     180
agttcacgga gggggagaga aagggagcac tttaaaagtt gaggtcccag tattcactct     240
taacagtgat gatccagaag atagatggaa tttttcagta ttctgtcttc ggattgctgt     300
tagtgaggat gccaacaaac cgctcaggca aggtgctctc atatccctct tatgctccca     360
ttctcaagtg atgagaaacc atgttgccct tgcagggaaa cagaatgaag ccacattggc     420
tattcttgag atcgacagtt ttaccaacag tgtgcctcag ttcaacaaca ggagcggagt     480
gtctgaagag agagcacaga gattcatggt gatagcagag tctctccccc gggcatgcag     540
taacaatact ccgttcgtta cagctggagt tgaaaatgat gtgccagaag atatcactga     600
cactctggaa agaatcttat ctatccaggc tcaggtatgg gtcacagtag caaaggcaat     660
gactgcatat gagacagcag atgagtcaga acaagaagg atcaacaagt atatgcagca     720
aggtagggtc cagaagaagt acatcctcca tcccgtatgc aggagtgcaa ttcaactcac     780
aatcagacat tctctagcag tccgcatttt tttagttagt gagcttaaga ggggccgcaa     840
tacggcaggt gggagttcca cgtattacaa cttagttggg gatgtagact catacataag     900
gaacaccggg cttactgcat tcttcctgac actcaagtat ggaatcaata ccaagacatc     960
agcccttgca ctcagcagcc tcacaggtga tatccaaaaa atgaaacagc tcatgcgttt    1020
atatcggatg aaaggagaaa atgcaccgta catgacattg ctaggtgaca gcgaccagat    1080
gagcttcgca ccagctgaat atgcacaact ctactctttt gccatgggca tggcatcagt    1140
cttagatagg ggaactggta ataccaatt cgccagagac ttcatgagta catcattctg    1200
gagactcggg gtggagtatg ctcaggctca gggaagcagc atcaatgagg atatggctgc    1260
tgaattgaag ctaactccag cagcaaggag gggcctggca gctgctgccc aacgagtatc    1320
tgaggaaatt ggcaatatgg atattcctac tcaacaggcc ggggtcctta ctgggctcag    1380
cgacaaaggt ccccgagctc gcagggtgg accgagcagg tcgcaagggc aaccggatgc    1440
tggggatggg gagacccaat tcttagacct gatgagagca gtggcaaaca gcatgcgaga    1500
agcgccagat tctgcacaga gcaccattca cccggagcct ctcccaactc atgtgccacc    1560
ccaggacaac gacaccgact gggggtactg atcgacagca cccagcctgc cctcacagaa    1620
ccatctcaaa ccatccgctg gaatcctccc caaactccac aactcaccgg ctcacgcagc    1680
caaaccagca ggagcatccc ccaaatcccc ccccacccc cagccacacg gccccgcccg    1740
cccagaacaa cacgggcaca acccaatcca ccaacaatcc gcacagaacc caaaatatta    1800
gaaaaaaata cgggtagaag agagacatcc agagatcagg acgagccacc aagatctcca    1860
ctctcccctc cacccagcga accagggcaa agatggccac cttcaccgat gctgagatag    1920
aggatatatt tgagaccagt ggaactgtca ttgacagtat aatcacagcc cagggtagat    1980
cagcagagac tgtcgggaag agcgcaatcc cgcaaggcaa gacaaaggcc ctgagcacag    2040
cacgggagaa gcacggagc atccagccat ccgccggcca ggacaccccc aaccaacaag    2100
acaaaccaga caaacagcca cccgcatccg agcaggtgac tccacacaac gatccctga    2160
```

```
ccgcacccaa agaacctctc cccactcagg ctgcaggtga tgctggcgac acacagctca    2220
agaccggagc aagcaactct cttttgtcaa tgcttgacaa gctgagcaac aaatcgtcta    2280
atgctaaaaa agggccaagg tcgatccccc aggagagtca tcatcaacct ccggcccaac    2340
aacacgggaa tcaggcgagc cgcggaaaca accaggaagg accgcagctt caggccaaag    2400
ctgcccctgg aagccggggc acagacgcga gcacagcata tcatggacaa tggaaggagt    2460
cacaactatc agctggtgca acccctcatg tgctccagtc agggcggagc caagacagta    2520
ctcctgtacc tgtggagcat gtccaactac ctgtcgactt tgtgcaggcg atgatgtcta    2580
tgatggaggc gttatcacag aaggtaagta aaattgacta tcagctagac ctagtctcaa    2640
agcagacatc ctctatccct atgatgcgat ctgaaatcca acagcttaaa acatctgttg    2700
caatcatgga ggccaattta ggcatgatga aaattctgga ccctggttgt gccaacattt    2760
cgtccttaag tgatctacga gcagttgctc gatcccatcc agttttagtt tcgggccccg    2820
gagatccatc cctttacgtg acacagaggg gtgaaatgac actcaataaa ctctcgcaac    2880
cggtacagca tccttctgag ttaattaaat ctgccatggt aagcgggccc gatatgggag    2940
tggagaagga cactgtccgt gcattaatca catcgcgccc gatgcatcca agctcctcgg    3000
ctaagctcct gagtaagttg gacgcggcca gtcgatcga agagatcaga aaggtcaagc    3060
gccttgcgct gaatggttga tagccatcac agcttacgac aggctcttgc ctcaccagtg    3120
tcacaaggaa tctttctcaa accctccctc acagacctgc gccccaactt agaaaaaata    3180
cgggtagaaa ccatgaatgt caaaggaaga gtggttctgt caatgctgct tgtctcaact    3240
gtaatggttg tgttttggga atacatcaac agcccagaag gttctttgtt ctggatatac    3300
cagtcaaaaa acccagaagt tggcagcagt gctcagaggg gctggtggtt tccgagctgg    3360
tttaacaatg ggactcacag ttaccacgaa gaagaagacg ctataggcaa cgaaaaggaa    3420
caaagaaaag aagacaacag aggagagctt ccgctagtgg actggtttaa tcctgagaaa    3480
cgcccagagg tcgtgaccat aaccagatgg aaggctccag tggtatggga aggcacttac    3540
aacagagccg tcttagataa ttattatgcc aaacagaaaa ttaccgtggg cttgacggtt    3600
tttgctgtcg gaagatacat tgagcattac ttggaggagt tcttaatatc tgcaaataca    3660
tacttcatgg ttggccacaa agtcatcttt tacatcatgg tggatgatat ctccaggatg    3720
cctttgatag agctgggtcc tctgcgttcc tttaaagtgt ttgagatcaa gtccgagaag    3780
aggtggcaag acatcagcat gatgcgcatg aagaccatcg gggagcacat cctggcccac    3840
atccagcacg aggtggactt cctcttctgc atggacgtgg atcaggtctt ccaaacaaac    3900
tttggggtgg agaccctggg ccagtcggtg gctcagctac aggcctggtg gtacaaggca    3960
catcctgacg agttcaccta cgagaggcgg aaggagtccg cagcctacat tccgtttggc    4020 caggggatt tttattacca cgcagccatt tttgggggaa cacccactca ggttctaaac    4080
atcactcagg agtgcttcaa gggaatcctc caggacaagg aaaatgacat agaagccgag    4140
tggcatgatg aaagccatct aaacaagtat ttccttctca acaaacccac taaaatctta    4200
tccccagaat actgctggga ttatcatata ggcatgtctg tggatattag gattgtcaag    4260
atagcttggc agaaaaaaga gtataatttg gttagaaata acatctgaac ccccagcaac    4320
gaccctctct caccectctc actccccga gtgaccgcgt aactgcaatc agtctaacag    4380
cattggagat taagaaaaaa tacgggtaga atcaaagtac cccaattgtg caaaaatgga    4440
ctcatccaga acaatcaggc tgtactttga ttctgcccta ccttccagca gcctgttagc    4500
```

```
attcccgatc gtcctacaag gcacaggaga tgggaagaag cgaatcaccc cacaatacag    4560
gatccagcgt cttgacttgt ggacagacag caaggaagac tcagtattta tcaccaccta    4620
cggattcatc ttccaaattg ggaatgagga ggtcaccgtt ggcacgatca gtgacaatcc    4680
cagacatgag ctactttcct ctgcaatgct ctgcctagga agtgtcccaa atgacggaga    4740
tcttgttgaa ctggcaagag cctgcctcac catggtgata acttgtaaga agagtgcaac    4800
taatactgag agaatagtct tctcaatagt gcaggcacct cgagtgctgc aaagctgtat    4860
ggttgtggca aataagtact catcagtgaa tgcagtgaag catgtgaaag cacccgaaaa    4920
gatccctggg agcgggaccc tagagtataa agtgaatttc gtctctctga ctgtagtgcc    4980
gaggaaggat gtctacagga tcccaactgc agcattgaaa atctctggtt caagcctgta    5040
taatctcgcg ctcaatgtca ctattgatgt ggaggtagac ccgaagagcc cgctagtcaa    5100
atccctttct aagtctgata gcggatacta tgctaatctt tttttgcata tcgggcttat    5160
gcctactgta gataagaagg gaaagaaagt gacattcgac aagatagaag aaaagataag    5220
gagactcaat ctttctgtcg ggctcagtga tgtactcgga ccttctgtgc ttgtaaaggc    5280 gagggggtgca cggactaagc tactagcacc ttttttctct agcagcggga cggcctgcta    5340
tcctatagca aatgcctctc ctcaggttgc taagatactc tggagtcaaa ctgcgcacct    5400
gcgaagtgta aaagtcatca ttcaagcagg cacccaacgt gctgtcgcag tgactgctga    5460
ccatgaggtc acctctacta agatagagaa gaggcacacc atcgccaagt acaatccttt    5520
taagaagtaa gttgcatctc tgagactgcg agccacccac ttttccgaat catcacgaca    5580
ttagataatg atctatctta attgcttata gttagtttac ctgtctatct aattagaaaa    5640
aacacgggta gaagagtctg atcccagctg gcacatcca aagtgcaaca tgggctccaa    5700
accccacacc aggatcccag cacctctgat gctgatcacc cgaattactc tggtactgag    5760
ctgcatctgc ctgacgagtt ctcttgacgg caggccactt gcagctgcgg ggattgtggt    5820
aacaggagat aaagcaatca atatatacac ctcatctcag acagggtcaa tcatagtcaa    5880
gttgctcccg aatatgccca aggataagga ggcatgtgcg aaagcccgt tagaggcata    5940 caacagaaca ctgaccactt tactcacccc ccttggtgat tccatccgca ggatacaagg    6000
atctgtgtcc acatcaggag gaaggaggcg aaagcgcttc ataggtgcca ttacaggcag    6060
tgtagctctt ggggtagcga catcggcaca gataacagcg gctgcggccc taatacaagc    6120
caaccagaat gccgccaaca tcctccggct taaggagagc atcgctgcaa ccaatgaagc    6180
tgtgcatgag gtcactgacg gattgtcgca actagcagtg gcagttggga agatgcaaca    6240
gtttgtcaat gaccaattta ataatacagt gcgagaattg gactgtataa aaattacaca    6300
acaagtcggc atagaactca acctatacct aactgaactg actacagtgt tcgggccaca    6360
aatcacttcc cctgccttaa ctcagctgac catccaagcg ctttataatt tagctggcgg    6420
caacatggat tacttattga ctaaattagg tataggaac aatcatctca gctcattaat    6480
aggcagtggc ttgatcacag gcaatcctat actgtatgac tcacagactc aactcttggg    6540
catccaggta aatttaccct cagtcgggag ccttaataat atgcgtgcca cctacctgga    6600
gactttatct gtaagcacaa ccaaaggatt tgcctcagca cttgtcccga aggtagtgac    6660
acaagttggc tctgtgatag aagaactcga cacctcatac tgtatagagt ctgatctgga    6720
tttatactgt acaaggatag tgacattccc catgtctcca ggtatttatt cttgtctgag    6780
cggcaataca tcagcctgca tgtattcaaa gactgaaggc gcactcaata tcgccatcat    6840
ggtcctcaaa ggctcagtca ttgccaattg caaaatacaa acttgcaggt gtgcagaccc    6900
```

```
cccgggtatc atatcgcaaa attatggaga agctgtatct ctgatagata gacattcatg   6960
caatgtctta tcattagacg gggtaactct gaggctcagt ggggagtttg atgcaactta   7020
tcaaaagaat atctcaatac tagattctca agtcatcgtg acaggcaacc ttgatatatc   7080
aaccgagctt ggaaatgtca ataattcaat aagcaatgcc ctggataggt tagctgaaag   7140
taacagcaaa ctagacaaag tcaatgtcaa attaaccagc acatctgctc tcgttaccta   7200
tatcgttcta accgtcatat ctcttgtttt cggtgcactt agcatggttt tagcatgcta   7260
cctgatgtac aaacaaaagg cacaacaaaa gaccttactg tggcttggga caacaccct   7320
cgatcagatg agagccacta caagaacatg aatgcagacg agatacggat gtgtcctaaa   7380
caacaacttg tgtgtcaact ctgacaacct gctcaatgga agatttaaga aaaaactact   7440
ggatataaga aactgataag caatacacgg gtagaacggt cggggaggcc atcttccaat   7500
cgggaactag gcttcacaat atccgttcca ccacaccacc aacatcagat ttcagccatg   7560
gaccatgcag tcagcaaagt tgcgttagaa aatgaagaaa gagaagcgaa gagcacatgg   7620
cgcttggttt tccggatcgc agttttactt ttaatagtgg tgaccctagc catctctgta   7680
gctgccctgg tatacagcat gggggctagt acgccccgcg acctcgtagg catatcgact   7740
atggtttcta aggcggagga caggattacg tctttactca gttcgaacca agatgtagta   7800
gacagagtat acaagcaagt ggcccttgaa tctccgttgg cactactgaa tactgaatct   7860
ataatcatga atgcaataac gtctctctct catcaaatta acggggctgc aaacaatagc   7920
aggtgtgggg cgcctgttca tgacccagat tatatcgggg ggataggtaa agaactcata   7980
gtagacgacg tcagtggtgt cacatcattc tacccatctg cataccaaga acacctgaat   8040
tttatcccag cgcccactac aggatcaggc tgcactcgga taccctcatt tgatatgagt   8100
gctacccact actgttatac tcataacgtg atattgtcag gctgtataga tcactcacat   8160
tcacatcaat acctagcact tggtgtgctt cggacatcgg caacagggag ggtattcttt   8220
tctactctac gttccatcaa cttagatgac acccaaaatc ggaaatcttg cagtgtgagt   8280
gcaactcctc taggctgtga tatgctgtgc tctaaagtca cagaggctga agaagaggac   8340
tataagtcag ttaccccac atcaatggtg cacggaaggt taggttttga cggtcaatac   8400
catgagaaag acttagacac cacagtctta tttaaggatt gggtggcaaa ttacccggga   8460
gtggggagtg gatcttttat taatgaccgt gtatggttcc cagtttacgg agggttgaaa   8520
cctaattcgc ctagcgacac agcgcaagaa gggaaatatg taatatacaa gcgctataat   8580
aacacatgcc ctgatggaca ggaatatcaa atccggatgg ctaagtcttc gtacaagcct   8640
gggcgatttg gtggaaagcg tgtacagcaa gccattttat ccatcaaagt gtcaacatct   8700
ttgggtgagg atccagtgct gactgttccg cctaatacaa ttacactcat gggggccgaa   8760
ggcagggttc tcacagtagg gacatctcac ttcttatacc aacgagggtc ttcgtatttc   8820
tcccctgcct tattatatcc tatgacagtt tataacaaaa cagccactct tcataatcct   8880
tatacattta atgctttcac caggccaggt agtgtcccctt gtcaggcatc agcaagatgc   8940
cccaacccat gtatcactgg agtctatact gatccgtacc ctttggtctt ctataggaac   9000
catacccttgc gagggtctt cggaacaatg cttgatgatg aacaagcaag actcaacccc   9060
gtatctgcag tattcgacaa catatctcgc agtcgtgtga cccgagtaag ctcaagcagc   9120
accaaggcag catacacgac atcgacatgt ttcaaagttg tcaagaccaa taaagtttat   9180
tgtcttagca ttgcagaaat atctaacacc ctatttgggg aattcagaat cgttcctttg   9240
```

```
ttagttgaga ttctaaagga tgatagggtt taagaagcta gatctggtta gttgggtcga      9300
atgcagggtg gctgggaaga tgatactgta tcacctatct ctcgcaacac caaggatcaa      9360
actggatacc aatgcaagcc tgaatcccat accatcagac aggcaaaacc tgacaatgct      9420
gatgtgatca gtctgaattt tgtctgcagt caatttatta agaaaaaata tggatggcag      9480
tgaaatacag gggaaaacaa catacaaagg acagcacggg taggaaatgg cgagctccgg      9540
tcctgaaaga gcagaacatc agatcatcct accagagtca catctatcct ccccattagt      9600
caagcacaaa ctgctctact actggaaatt aactgggcta ccactccccg acgaatgcga      9660
ctttgatcat ctcattatca gcaggcaatg aagaaaaata cttgagtctg ccactcccga      9720
tactgagaga atgataaaac tcggacgggc agtgcatcag actctcaacc acaattccaa      9780
gataaccgga gtcctccatc ctaggtgttt agaagaactg tcaagtattg aggtccctga      9840
ttcaaccaac aaatttcgga agatcgaaaa gaagatccaa attcacaaca cgaggtacgg      9900
agacctgttc gccaggctgt gcgcgcatgt cgagaagaaa ttgctaggat catcccgatc      9960
tagcaaagtc tcacgatcag aggagttcag cagcatccta tcagatccag cattctggtt     10020
tcactcaaaa tggtccaggg ccaagtttgc atggctccat ataaaacaga tccagaggca     10080
tctgattgta gcagcaagaa caaggtctgc agtcaacaag ttagtgacat taacccataa     10140
gataggccaa gtctttgtta ctcctgagct cgtcattgtg actcatacgg atgagaacaa     10200
gtttacatgc ctcacccaag aacttgtatt gatgtatgca gatatgatgg agggcaggga     10260
catggtcagc ataatatcat ctacagcgac acatctcaga aatctatcag agaaaattga     10320
tgatattctg cggttagtag atgccctgtc aaaggatttg gcaatcaag tctatgatgt      10380 cgtagcattg atggagggat ttgcatatgg tgctgttcag ctgcttgagc cgtcaggtac     10440
attcgcagga gatttctttg cattcaacct gcaggagctc aaagacactc taatcgaact     10500
cctccccaat gatatagcgg aatcagtaac tcacgcaatt gcctccatat tctctggctt     10560
agaacaaaat caagcagctg agatgttgtg cttgttgcgt ttgtgggggtc acccactact     10620 tgagtcccgt agtgcagcaa agcagtcag gagccagatg tgcgcaccta aatggtaga     10680 cctttgatatg atcctccaag tattatcctt ctttaaggga acaatcatca atggatacag     10740
gaagaagaat tcaggtgtgt ggccacgagt caagatagat acgatatacg ggaaggtcat     10800
cgggcagcta catgctgact cagcggagat ttcacatgat gtcatgttga gagagtacaa     10860
aagtttatct gcccttgaat ttgagccatg tatagactat gaccctgtca ccaatctaag     10920 catgtttta aaggacaagg caatcgcaca tccgagagat aactggctcg cctcatttag     10980
gcggaacctt ctctctgagg accagaagaa acaggtgaag gaggcaacct caactaaccg     11040
cctcttgata gagttcctag aatcaaatga ttttgatcca tataaagaga tggaatactt     11100
gacaacccct gagtacctaa gagatgacag tgtggcggta tcgtactcac tcaaggagaa     11160
ggaggtgaag gttaatggc ggattttcgc caagttgaca aagaaattaa ggaactgcca     11220
ggtaatggca gaagggattc tagctgacca gattgcacct ttttccagg gaaatggggt     11280 cattcaagat agcatatcct tgaccaagag tatgttagcg atgagtcaac tgtctttaa      11340 cagcaacagg aaacgtatca ctgactgcaa ggagagggtc tcctcaaacc gcaatcacga     11400
tccaaagagc aagaatcgtc gaagagttgc cactttttatc acgactgact tgcaaaagta     11460 ttgtctaac tggagatatc agacggttaa gctattcgcc catgctatca atcagctaat     11520
gggcctacct cacttcttcg agtggattca cctcagatta atggacacta caatgttgt      11580 aggagacccc ttcaatcctc caagtgaccc gaccgactgt gatctatcaa gagtcccaaa     11640
```

```
tgatgatata tatattgtca gtgctagagg aggcattgag ggattatgcc agaagctatg   11700
gacaatgatc tcaattgctg caatccaact tgctgcagca agatcgcatt gccgagttgc   11760
ctgcatggta caaggtgaca atcaagtaat agctgtaaca agagaagtaa gatcagatga   11820
ctccccagat atggtgttga cacagttgca tcaagctagt gataatttct tcaaagaact   11880
gattcacgtc aatcatctga tcggtcacaa cctgaaagat cgtgaaacca tcaggtcaga   11940
cacattcttc atatacagca agcggatatt caaagacgga gcaatactca gtcaggtcct   12000
caaaaactca tctaaattgg tgctgatatc aggagacctt agtgaaaaca ctgtaatgtc   12060
ctgtgccaac attgcatcca ctgtagcacg gctatgtgag aacgggcttc ctaaggactt   12120
ctgttattat ttaaactacc taatgagttg tgtgcagaca tattttgatt cagaattttc   12180
tattactcac agctcgcagc cggattccaa ccagtcttgg attgaggaca tctcttttgt   12240
ccactcgtat gtcttaaccc ctgcccagct aggaggactg agtaaccttc aatactcaag   12300
actctataca aggaatattg gtgacccggg gactactgct tttgcagagg tcaagcgatt   12360
agaagcagtg gggttgctga gtcctagcat tatgactaat atcttaacta ggccacctgg   12420
caatggtgac tgggccagcc tgtgcaacga tccttactca tttaattttg agactgttgc   12480
aagcccaaat attgtcctta agaaacacac acagaaagtc ttatttgaga cttgttcaaa   12540
ccctttatta tcaggagtac acacagagga caatgaggca gaagagaagg cattggctga   12600
attcctactc aatcaagaag cggttcaccc acgtgtcgca catgctatca tggaagcaag   12660
ctctgtaggt aggagaaagc agattcaagg acttgttgac actacaaaca ctgtgattaa   12720
gattgcactg accaggagac ccctcggtat caagaggctg acacggataa tcaattactc   12780
gagcatgcat gcaatgttat tcagagatga tgtcttcttg cctaagagat ccaaccaccc   12840
attagtttcg tctgctatgt gctcgctgac actagcagac tatgcccgga acagaagctg   12900 gtcacccttta acaggggggta ggaagatact aggtgtatct aacccccgata ccatagaact   12960 tgtagaggga gagatcctta gtgtcagtgg gggatgcaca aaatgtgaca gcggagatga   13020
acagtttact tggtttcatc ttccaagcaa tatagagctg actgacgaca ccagcaagaa   13080
tcctccaatg agagtgccgt atcttgggtc aaagacccaa gagaggaggg ctgcctcact   13140
tgcgaaaata gctcatatgt cgccacatgt gaaggcagca ttaagggcat catctgtgtt   13200
aatctgggct tacgggggaca acgaagttaa ttggactgct gctcttaaga ttgcaaggtc   13260
tcgatgcaac ataagctcag agtatcttcg gctactgtca cccctgccca cagctgggaa   13320
tctccaacat agattggatg atggcataac ccagatgaca tttaccccctg catctctcta   13380 cagagtatca ccttacattc acatatccaa tgattcccaa agactattta ctgaagaagg   13440
aatcaaagaa gggaatgtgg tttatcaaca aattatgctc ctgggcctat ccctaattga   13500
atcactcttc ccgatgacaa caaccaagac ttatgatgag atcacattac acctccacag   13560
taaatttagc tgctgtatca gggaagcgcc tgttgctgtc cccttcgagt tactcgggat   13620
ggcaccagaa ttaaggacgg taacctcaaa taagttcatg tatgatccta gccctatatc   13680
agagagagat tttgcgagac ttgacttggc tatcttcaag agttacgagc ttaatttaga   13740
gtcatattcc acaatggaac taatgaacat tctttcaata tctagcggga agttgattgg   13800
acagtctgtg gtttcctatg atgaagatac ttctataaag aatgatgcta taatagtgta   13860
tgataacaca cgaaattgga ttagtgaagc acagaattca gatgtggttc gcctattcga   13920
gtatgcagcg cttgaagtgc tcctcgactg ttcttaccaa ctctactatc tgagagtgag   13980
```

```
aggtctcaac aacatcgtcc tatacatgag tgacttatac aagaatatgc cagggatttt    14040
actctctaac attgcggcta caatttctca tcccattatt cactcaaggt tgaatgcagt    14100
aggtctggtc aaccatgacg ggtcacacca gcttgcagac acagatttca ttgaaatgtc    14160
tgcgaaattg ttagtctctt gcactcgacg cgtggtctca ggattatatg cggggaataa    14220
gtacgatctg ctgttcccat ctgttctgga tgataacctg agtgagaaga tgtttcagct    14280
gatttcccgg ttatgctgtc tgtatacagt acttttttgct acaacaagag agatcccaaa   14340 aataagggc ctgtcagcgg aagagaaatg ctcagtactc actgagtacc tattgtcgga    14400
tgctgtgaaa ccattgctta aatccgaaca agtgagctct attatgtctc caacataat     14460 tacgttccca gccaatctat attacatgtc taggaagagc cttaatttaa tcagggagcg    14520
agaggacaga gatgccattc tggcgttgtt gttcccccaa gaaccactgc tcgagcttcg    14580
tccagttcaa gacattggtg ctcgagtgag agatcctttc actcaacaac ctgcatcatt    14640
catacaagaa ctagatctga gtgctccagc aaggtatgat gcatttactc ttagtgaagt    14700
tcgccctgag cacacattgc cgaacccaga gaggattac ttagtacggt atttgttcag     14760
aggaataggg actgcttcat cttcttggta taaggtatct catcttcttt ctgtccctga    14820
ggtcaaatgt gcaagacatg ggaactcctt atacttggca gaaggaagtg gagccatcat    14880
gagtattctt gagctgcata taccacacga gaccatctat tacaatacac ttttctcgaa    14940
tgagatgaac cccccacagc gacatttcgg accgacccca acacagtttc taaattcagt    15000
cgtttatagg aatctacagg cggaagtgcc atgcaaagat ggatttgtcc aggagttctg    15060
cccattatgg agagagaatg cagaagaaag tgacttgacc tcagataagg cagtgggata    15120
catcacatcc gtggtgccct ataggtctgt ttcattatta cattgtgaca ttgaaattcc    15180
tccagggtcc agtcaaagcc tgttagacca actggctact aatttatctt tgattgccat    15240
gcactctgta agggagggtg gagtagtgat catcaaagta ctatatgtaa tgggatacta    15300
ctttcatcta ctcgtgaatt tgttcactcc gtgttccaca aaaggatata ttctctctaa    15360
tggatatgcc tgtagagggg atatggagtg ttacctgata tttgtcatgg gctatctagg    15420
cgggcctaca ttcgtaaatg aagtagtgag gatggcaaaa actctaatac aacagcacgg    15480
tacacttctg tctaaatcgg atgagattaa gttaactaag ctatttacct cacagcagca    15540
tcgtgtagta gacatccttt ccagcccttt accgagacta atgaagtatt tgagagaaaa    15600
tatcgatgct gcactgattg aggctggggg acagcccgtc cgcccattct gtgcagagag    15660
tttagtgggc acattgacag atatgactca gatggctcag atcattgcca gccacattga    15720
cacagttatt cgatctgtga tttacatgga ggctgagggt gaccttgctg acacagtgtt    15780
cctgtttact ccttacaatc tctctacaga cggtaagaag agaacatcac tcaaacagtg    15840
cacaaggcag atcctagagg tcactatatt ggggctcaga gccagagatc tcaacaaaat    15900
aggtgatgta ataggcttaa tactcaaagg tatggtttct ctggaggacc tcatcccact    15960
aaggacatac ctgaagcaca gtacatgccc gaagtatttg aaggcagtcc tcggaattac    16020
taaactcaaa gagatgttta cagaaacctc tttactatac ttgactcgtg ctcaacaaaa    16080
attctacatg aaaaccatag gtaatgcagc caagggatat tacagtaaca atgactccta    16140
aaggcaatct tacgttaatg aattatctcc ctaattgact gctccctcat tgctttgata    16200
gtaccgtatt agaaaaaagt taaattctga tcttttgaag ctcgtgttcg ggttcaagca    16260
```

```
attatcttaa agcagcagtg aacgtggttg tccttaatta tagtcttgtc attcaccaaa    16320
tctttgtttg gt                                                        16332
```

UNITED STATES PATENT AND TRADEMARK OFFICE
CERTIFICATE OF CORRECTION

PATENT NO. : 10,080,797 B2
APPLICATION NO. : 15/244006
DATED : September 25, 2018
INVENTOR(S) : Yongxiang et al.

Page 1 of 1

It is certified that error appears in the above-identified patent and that said Letters Patent is hereby corrected as shown below:

On the Title Page

Item (72):
"Yongxiang Zhao" should be added as the first inventor.

Item (72) Inventors is corrected to read:
-- Yongxiang Zhao, Hunan (CN);
Xia Peng, Hunan (CN);
Yi Peng, Guangxi (CN); --.

Signed and Sealed this
Twenty-eighth Day of January, 2020

Andrei Iancu
*Director of the United States Patent and Trademark Office*